United States Patent
Nebolsin et al.

(10) Patent No.: US 11,439,631 B2
(45) Date of Patent: Sep. 13, 2022

(54) USE OF A GLUTARIMIDE DERIVATIVE TO TREAT DISEASES RELATED TO THE ABERRANT ACTIVITY OF CYTOKINES

(71) Applicant: "CHEMIMMUNE THERAPEUTICS" LIMITED LIABILITY COMPANY, Moscow (RU)

(72) Inventors: Vladimir Evgenievich Nebolsin, Moskovskaya obl (RU); Anastasia Vladimirovna Rydlovskaya, St. Petersburg (RU)

(73) Assignee: "CHEMIMMUNE THERAPEUTICS" LIMITED LIABILITY COMPANY, Moscow (RU)

( * ) Notice: Subject to any disclaimer, the term of this patent is extended or adjusted under 35 U.S.C. 154(b) by 0 days.

(21) Appl. No.: 16/644,899

(22) PCT Filed: Mar. 6, 2018

(86) PCT No.: PCT/RU2018/000135
§ 371 (c)(1),
(2) Date: Mar. 5, 2020

(87) PCT Pub. No.: WO2019/050429
PCT Pub. Date: Mar. 14, 2019

(65) Prior Publication Data
US 2020/0188379 A1   Jun. 18, 2020

(30) Foreign Application Priority Data
Sep. 7, 2017  (RU) .................. 2017131435

(51) Int. Cl.
A61K 31/454   (2006.01)
A61P 29/00    (2006.01)

(52) U.S. Cl.
CPC .......... *A61K 31/454* (2013.01); *A61P 29/00* (2018.01)

(58) Field of Classification Search
CPC ........ A61K 31/454; A61P 29/00; A61P 11/00; A61P 17/06; A61P 19/02
USPC ...................................................... 514/326
See application file for complete search history.

(56) References Cited

U.S. PATENT DOCUMENTS 10,155,743 B2 * 12/2018 Nebolsin .......... A61P 11/00
2016/0046898 A1 * 2/2016 Lee .................. C12M 23/20
                                                435/299.1

FOREIGN PATENT DOCUMENTS

| EP | 2985282 A1 | 2/2016 |
| RU | 2278857 C2 | 6/2006 |
| RU | 2552929 C1 | 6/2015 |
| RU | 2562773 C2 | 9/2015 |
| WO | WO-2014168522 A9 | 1/2015 |

OTHER PUBLICATIONS

Wikipedia , Upper Respiratory Tract Infection, Apr. 2015, p. 1-7 (Year: 2015).*
Cynis et al. (2008). "Isolation of an isoenzyme of human glutaminyl cyclase: retention in the Golgi complex suggests involvement in the protein maturation machinery.", J Mol Biol., 379 (5): 966-80.
Cynis et al. (2011). "The isoenzyme of glutaminyl cyclase is an important regulator of monocyte infiltration under inflammatory conditions.", EMBO Mol Med., 3 (9): 545-58.
D'Haese et al. (2010). "Fractalkine/CX3CR1: why a single chemokine-receptor duo bears a major and unique therapeutic potential.", Expert Opin Ther Targets., 14(2):207-19.
Huang et al. (2011). "Structures of human Golgi-resident glutaminyl cyclase and its complexes with inhibitors reveal a large loop movement upon inhibitor binding.", J Biol Chem, 286 (14): 12439-49.
International Search Report received for PCT Patent Application No. PCT/RU2018/000135, dated Aug. 2, 2018, 3 pages.
Kehlen et al. (2017). "N-terminal pyroglutamate formation in CX3CL1 is essential for its full biologic activity.", Biosci Rep. ,37(4): 1-14.
Lee et al. (2013). "Simvastatin suppresses RANTES-mediated neutrophilia in polyinosinic-polycytidylic acid-induced pneumonia. ", Eur Respir J., 41(5):1147-1156.
Mercer et al. (2014). "Proteinase-activated receptor-1, CCL2, and CCL7 regulate acute neutrophilic lung inflammation.", Am J Respir Cell Mol Biol., 50(1):144-57.

(Continued)

*Primary Examiner* — Taylor V Oh
(74) *Attorney, Agent, or Firm* — BCF LLP

(57) ABSTRACT

The invention relates to medicine and concerns the treatment of diseases related to the aberrant activity of fractalkine and monocyte chemoattractant proteins 1-4 (CCL2, CCL7, CCL8, CCL13), preferably the treatment of pain, fever, pneumonia, bronchitis, bronchiolitis, alveolitis, rheumatoid arthritis, psoriasis and other diseases, using the compound 1-(2-(1H-imidazol-4-yl)ethyl)piperidine-2,6-dione

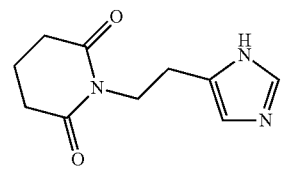

or a pharmaceutically acceptable salt or solvate thereof
The present invention also relates to pharmaceutical compositions that contain a therapeutically effective amount of the claimed compound according to the invention. The present compound and pharmaceutically acceptable salts thereof are highly effective in inhibiting the activity of the glutaminyl cyclase enzyme, which is involved in particular in processes of post-translational modification of the above-mentioned cytokines.

5 Claims, No Drawings

(56) References Cited

OTHER PUBLICATIONS

Schilling et al. (2003). "Identification of human glutaminyl cyclase as a metalloenzyme. Potent inhibition by imidazole derivatives and heterocyclic chelators.", J Biol Chem, 278 (50): 49773-9.

Schilling et al. (2004). "Glutaminyl cyclases unfold glutamyl cyclase activity under mild acid conditions.", FEBS Lett., 563 (1-3): 191-6.

Silverpil et al. (2012). "IL-17 in human asthma.", Expert Rev. Respir. Med. 6(2)173-186.

Tomazzeti et al. (2005). "Baker's yeast-induced fever in young rats: characterization and validation of an animal model for antipyretics screening.", J. Neurosci Methods. 147:29-35.

Wong C.K. (2010). "Interleukin-17A activation on bronchial epithelium and basophils: a novel inflammatory mechanism.", Eur Respir J. 35:883-893.

Conjun et al., (2015). "Elevated Local and Serum CX3CL1 (Fractalkine) Expression and Its Association with Disease Severity in Patients with Psoriasis," Ann Clin Lab Sci., 45(5):556-61.

Nanki et al., (2016). "Fractalkine/CX3CL1 in rheumatoid arthritis," Modern Rheumatology, 27(3):392-397.

\* cited by examiner

USE OF A GLUTARIMIDE DERIVATIVE TO TREAT DISEASES RELATED TO THE ABERRANT ACTIVITY OF CYTOKINES

CROSS REFERENCE TO RELATED APPLICATIONS

This application is a national stage application under 35 U.S.C. § 371 of International Application No. PCT/RU2018/000135, filed internationally on Mar. 6, 2018, which claims priority of Russian Application No. 2017131435 filed on Sep. 7, 2017.

FIELD OF THE INVENTION

The invention relates to medicine and concerns the treatment of diseases related to the aberrant activity of fractalkine and monocyte chemoattractant proteins 1-4 (CCL2, CCL7, CCL8, CCL13), preferably the treatment of pain, fever, pneumonia, bronchitis, bronchiolitis, alveolitis, rheumatoid arthritis, psoriasis and also other diseases, using the compound that is effective in inhibiting an enzyme—glutaminyl cyclase, which is involved in particular in processes of post-translational modification of the abovementioned cytokines.

BACKGROUND OF THE INVENTION

Cytokines are a group of hormone-like proteins and peptides which are secreted by immune system cells and other types of cells and are involved in the control of the development and homeostasis of the immune system, the control of the growth and differentiation of blood cells (hemopoiesis system) and in nonspecific protective reactions of organism. The cytokines also take part in the regulation of growth, differentiation and life time of the cells, and in the control of apoptosis.

The cytokine production by mammalian cells is a complex and multi-stage process. Most cytokines (e.g., fractalkine and monocyte chemoattractant proteins) are expressed in the form of an inactive precursor, from which in the process of detachment of a signal peptide and the post-translational modification of individual amino acid residues of the protein an active form of the cytokine forms. One of the most important post-translational modifications is the cytokine N-terminal pyroglutamation. The pyroglutamation significantly increases the stability of hormones and chemokines containing the N-terminal residue of glutamine or glutamic acid. The pyroglutamation of the N-terminal residue is catalyzed by the enzyme—glutaminyl cyclase (QPCT or QC) [J Biol Chem 2003 Dec. 12; 278 (50): 49773-9; J Mol Biol. 2008 Jun. 20; 379 (5): 966-80]. Glutaminyl cyclase has the broad substrate specificity and is involved in the post-translational modification of a variety of peptide molecules. In particular, the well-studied substrates of glutaminyl cyclase are monocyte chemoattractant proteins (CCL2), CCL7, CCCL8, CCL13) [EMBO Mol Med. 2011 September; 3 (9): 545-58] and fractalkine [Biosci Rep. 2017 Aug. 23; 37 (4)]. It has been shown in studies of the substrate specificity of glutaminyl cyclase that the enzyme can catalyze the pyroglutamation of different substrates, regardless of the length of the polypeptide chain [FEBS Lett. 2004 Apr. 9; 563 (1-3): 191-6, J Biol Chem 2011 Apr. 8; 286 (14): 12439-49].

Since the pyroglutamation of the N-terminal residue mediated by glutaminyl cyclase significantly increases the stability of fractalkine and monocyte chemoattractant proteins, the strategy directed to the inhibition of glutaminyl cyclase is a possible approach to modulate the aberrant activity of these cytokines. Thus, glutaminyl cyclase inhibitors can obviously be used for the therapy of a wide range of diseases and, in particular, lower respiratory tract diseases such as pneumonia, bronchitis and bronchiolitis. The pathogenesis of these diseases is related to excessive biosynthesis of cytokines and, in particular, monocyte chemoattractant proteins CCCL2 and CCL7 [Am J Respir Cell Mol Biol. 2014 January; 50(1):144-57] and fractalkine [Expert Opin Ther Targets. 2010 February; 14(2):207-19.], which are glutaminyl cyclase substrates [Biosci Rep. 2017 Aug. 23;37 (4). pii: BSR20170712; EMBO Mol Med. 2011 September; 3(9):545-58]. It has been shown that the neutralization of CCL2 and CCL7 with the use of antibodies significantly reduces the influx of leukocytes, in particular neutrophils, to the lower respiratory tracts of experimental animals [Am J Respir Cell Mol Biol. 2014 January; 50(1):144-57]. The action of bacterial lipopolysaccharides, lipoteichoic acid or other stimuli on the mucous membrane of respiratory organs leads to the increase in secretion of monocyte chemoattractant protein CCL2 by cells of bronchial smooth muscles [Am J Physiol Lung Cell Mol Physiol. 2012 Apr. 15; 302(8):L785-92] and the increase in CCL2 concentration in bronchoalveolar lavage [Mol Immunol. 2011 July; 48(12-13):1468-76]. The increase in the CCL2 concentration, in turn, causes the migration of cells of the immune system (predominantly neutrophils and basophils) and the development of the aberrant response related to the release of a greater quantity of chemokines (TNFα, IL-1, IL-6) and active forms of oxygen which damage surrounding cells of respiratory organs, in particular, bronchi [Immunobiology. 2016 February; 221(2):182-7; Int J Biol Sci. 2012; 8(9): 1281-90; Mol Immunol. 2013 November; 56(1-2):57-63]. The damage of the lower divisions of respiratory tracts results in the development and maintenance of the increased activity of cells of the immune system and the further destruction of tissues of respiratory organs.

It is important to note that the CC2-mediated development of neutrophil inflammation and the development of the aberrant response related to the release of pyrogenic cytokines (IL-1, TNFα, IL-6) results in the increase in temperature and development of fever [J Infect Dis. 1999 March; 179 Suppl 2:S294-304; Front Biosci. 2004 May 1; 9:1433-49]. Thus, the inhibition of the activity of glutaminyl cyclase may result in the decrease in the CCL2 concentration, the decrease in the intensity of the aberrant immune response and the reduction of the intensity of fever and the normalization of temperature.

In addition to fever and elevated temperature, pain syndrome is also the extremely common symptom of various diseases. It is obvious that the reduction of the intensity of the aberrant response related to the release of the increased number of active forms of oxygen which damage surrounding tissues should in itself result in the decrease in the intensity of the pain syndrome. In recent work, the key role of fractalkine in the pathogenesis of chronic pain has been shown [J Neurochem. 2017 May; 141(4):520-531]. Glutaminyl cyclase inhibitors can be used for the therapy of various autoimmune diseases, in particular rheumatoid arthritis and psoriasis. Fractalkine is one of the key proinflammatory mediators involved in the development of autoimmune diseases. The interaction between fractalkine and its unique receptor (CX3CR1) induces the cell adhesion, chemotaxis and cell survival [Mol Interv. 2010 October; 10(5):263-70]. The fractalkine level is increased in patients with rheumatoid arthritis (PA) [Mod Rheumatol. 2017 May;

27(3):392-397], psoriasis [Ann Clin Lab Sci. 2015 Fall; 45(5):556-61] and correlates with the severity of disease. Fractalkine is expressed on fibroblast-like synoviocytes and endothelial cells in synovial tissue of patients with rheumatoid arthritis. In case of psoriasis, high levels of fractalkine production are observed in dermal papillae and antigen-presenting cells [Br J Dermatol. 2001 June; 144(6):1105-13]. The expression of fractalkine is enhanced by the tumor necrosis factor-α and interferon-γ, and in case of rheumatoid arthritis, promotes the migration of monocytes, T-cells and osteoclast precursors to the synovial tissue [Mod Rheumatol. 2017 May; 27(3):392-397]. The increased expression of fractalkine in dermal papillae explains the migration and accumulation of T-cells at these sites in case of psoriasis [Br J Dermatol. 2001 June; 144(6):1105-13]. Fractalkine also induces the formation of inflammatory mediators by macrophages, T-cells and fibroblast-like synoviocytes. Moreover, fractalkine promotes angiogenesis and osteoclastogenesis.

Thus, based on the literature data, it is possible to conclude that the strategy directed to the inhibition of glutaminyl cyclase is the possible approach to the treatment of pain syndrome, fever and a whole number of diseases such as pneumonia, bronchitis, bronchiolitis, alveolitis, rheumatoid arthritis and psoriasis.

However, so far there is no drug acting as the glutaminyl cyclase inhibitor, which would be used in the therapy of diseases related to the aberrant activity of fractalkine and monocyte chemoattractant proteins, therefore there remains a need for the development and the practical application of new effective drugs based on glutaminyl cyclase inhibitors.

The present invention relates to the use of a novel chemical compound which is the glutaminyl cyclase inhibitor and is effective in suppressing the aberrant activity of fractalkine and monocyte chemoattractant proteins, for the therapy of pain syndrome, fever, pneumonia, bronchitis, bronchiolitis, alveolitis, rheumatoid arthritis and psoriasis, as well as other diseases.

DISCLOSURE OF THE INVENTION

It is an object of the present invention to provide a novel medicament effective for the prevention and/or treatment of diseases related to the aberrant activity of fractalkine and monocyte chemoattractant proteins 1-4 (CCL2, CCL7, CCL8, CCL13), preferably, the therapy of pain syndrome, fever, pneumonia, bronchitis, bronchiolitis, alveolitis, rheumatoid arthritis and psoriasis, as well as other diseases.

The technical result of the invention is the development and production of an effective glutaminyl cyclase inhibitor having a high inhibitory activity, which makes it possible to use the inhibitor for the therapy of pain syndrome, fever, pneumonia, bronchitis, bronchiolitis, alveolitis, rheumatoid arthritis and psoriasis, as well as other diseases related to the aberrant activity of fractalkine and/or monocyte chemoattractant proteins 1-4 (CCL2, CCL7, CCL8, CCL13). Said therapeutic effect is achieved by the inhibition of the activity of the enzyme—glutaminyl cyclase, which may result in the suppression of the aberrant activity of fractalkine and monocyte chemoattractant proteins 1-4 (CCL2, CCL7, CCL8, CCL13), as well as the reduction of the concentration of the abovementioned cytokines in the pathological process development zone.

The indicated technical result is achieved by using the compound 1-(2-(1H-imidazol-4-yl)ethyl)piperidine-2,6-dione (Compound 1)

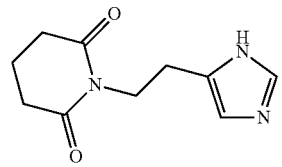 [SMILES: O=C1CCCC(=O)N1CCc1cnc[nH]1]

or a salt or solvate thereof as the compound suppressing the aberrant activity of fractalkine and monocyte chemoattractant proteins 1-4.

The indicated technical result is also achieved by using the compound 1-(2-(1H-imidazol-4-yl)ethyl)piperidine-2,6-dione or a salt or solvate thereof for preparing a medicinal agent for the prevention and/or treatment of a disorder related to the aberrant activity of fractalkine and monocyte chemoattractant proteins 1-4 (CCL2, CCL7, CCL8, CCL13).

The invention also includes a method of preventing and/or treating disorders related to the aberrant activity of fractalkine and monocyte chemoattractant proteins 1-4 (CCL2, CCL7, CCL8, CCL13) in the body, comprising administering to body an effective amount of 1-(2-(1H-imidazol-4-yl)ethyl)piperidine-2,6-dione or a pharmaceutically acceptable salt or solvate thereof. Such a disorder related to the activity of cytokines that are substrates of the enzyme—glutaminyl cyclase, in some non-limiting embodiments of the invention, is pain syndrome, fever, pneumonia, bronchitis, bronchiolitis, alveolitis, rheumatoid arthritis and psoriasis. In particular embodiments of the invention, the body is a body of a human or an animal.

Compound 1-(2-(1H-imidazol-4-yl)ethyl)piperidine-2,6-dione is described in the invention application WO 2014/168522.

In particular, the invention relates to a medicament for the prevention and/or treatment of a disease or condition related to the aberrant activity of fractalkine and monocyte chemoattractant proteins 1-4 (CCL2, CCL7, CCL8, CCL13), comprising as an active component 1-(2-(1H-imidazol-4-yl) ethyl)piperidine-2,6-dione:

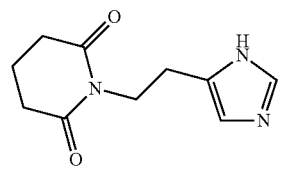 [SMILES: O=C1CCCC(=O)N1CCc1cnc[nH]1]

or a pharmaceutically acceptable salt or solvate thereof.

The disease to the treatment of which the medicament is directed is selected from the group consisting of pneumonia, bronchitis, bronchiolitis, alveolitis or autoimmune disease, in particular psoriasis or rheumatoid arthritis, as well as pain syndrome.

The condition to the treatment of which the medicament is directed is selected from the group consisting of fever and elevated temperature.

The active ingredient or a pharmaceutically acceptable salt or solvate thereof are present in an effective amount for the prevention and/or treatment of a disease or condition associate with the aberrant activity of fractalkine and monocyte chemoattractant proteins 1-4 (CCL2, CCL7, CCL8, CCL13). An amount of said active component in the medicament provides a dose thereof from 0.01 to 0.2 g for a patient per day.

Preferably, the amount of the active component in the medicament provides a dose thereof of 0.1 to 0.2 g for a patient per day.

Further, the invention comprises a method for preventing and/or treating a disease or condition related to the aberrant activity of fractalkine and monocyte chemoattractant proteins 1-4 (CCL2, CCL7, CCL8, CCL13) in a body, comprising administering to said body an effective amount of 1-(2-(1-imidazol-4-yl)ethyl)piperidine-2,6-dione:

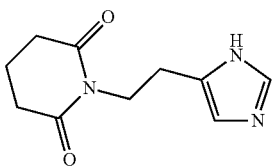 [SMILES: O=C1CCCC(=O)N1CCc1cnc[nH]1]

or a pharmaceutically acceptable salt or solvate thereof.

The disease to the treatment of which said method is directed is selected from the group consisting of pneumonia, bronchitis, bronchiolitis, alveolitis, autoimmune disease, in particular psoriasis or rheumatoid arthritis, and also pain syndrome.

The condition to the treatment of which the medicament is directed is selected from the group consisting of fever and elevated temperature.

A dose of 1-(2-(1H-imidazol-4-yl)ethyl)piperidine-2,6-dione or a pharmaceutically acceptable salt or solvate thereof, used in the method according to the invention, is from 0.01 to 0.2 g for a patient per day.

Preferably, the dose of 1-(2-(1H-imidazol-4-yl)ethyl)piperidine-2,6-dione or a pharmaceutically acceptable salt or solvate thereof, used in the method according to the invention, is from 0.1 to 0.2 g for a patient per day.

Further, the invention comprises the use of 1-(2-(1H-imidazol-4-yl)ethyl)piperidine-2,6-dione:

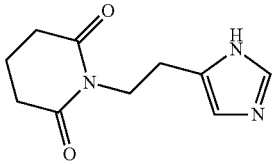 [SMILES: O=C1CCCC(=O)N1CCc1cnc[nH]1]

or a pharmaceutically acceptable salt or solvate thereof, in the manufacture of a medicament for the prevention and/or treatment of a disease or condition related to the aberrant activity of fractalkine and monocyte chemoattractant proteins 1-4 (CCL2, CCL7, CCL8, CCL13).

At the same time, the disease to the prevention and/or treatment of which the claimed invention is directed is selected from the group comprising pneumonia, bronchitis, bronchiolitis, alveolitis, autoimmune disease, in particular psoriasis or rheumatoid arthritis, and also pain syndrome.

The condition to the prevention and/or treatment of which the claimed invention is directed is selected from the group consisting of fever and elevated temperature.

An amount of 1-(2-(1H-imidazol-4-yl)ethyl))piperidine-2,6-dione or a pharmaceutically acceptable salt or solvate thereof in the medicament provides a dose thereof from 0.01 to 0.2 g for a patient per day.

Preferably, the amount of 1-(2-(1H-imidazol-4-yl)ethyl)piperidine-2,6-dione or a pharmaceutically acceptable salt or solvate thereof in said medicament provides a dose thereof from 0.1 to 0.2 g for a patient per day.

DETAILED DESCRIPTION OF THE INVENTION

The preparation of Compound 1 that is the object of the present invention is described in the patent application publication WO 2014/168522.

Studies of Compound 1 that is the object of the present invention in models of various diseases have allowed to establish that the use of Compound 1 significantly reduces the cytokine-mediated influx of immune system cells. Thus, it has been shown that Compound 1 affects the aberrant activity of various cytokines. The reduction of the aberrant activity of cytokines and the influx of immune system cells can be used in the therapy of a variety of diseases, in particular, lung and respiratory tract diseases such as pneumonia, acute and chronic bronchitis, bronchiolitis, alveolitis. The search of possible therapeutic targets using methods of computational chemistry, molecular modeling and in vitro tests on the enzyme preparation has allowed to reveal that the observed therapeutic effect of Compound 1 is related to the ability of the compound to suppress the glutaminyl cyclase activity.

Thus, Compound 1 has the previously unknown pharmacological activity related to the inhibition of the action of the enzyme—glutaminyl cyclase and the mediated influence on the biosynthesis and the activity of fractalkine and monocyte chemoattractant proteins 1-4 (CCL2, CCL7, CCL8, CCL13), which indicates the applicability of Compound 1 for the therapy of pain syndrome, fever, pneumonia, bronchitis, bronchiolitis, alveolitis, rheumatoid arthritis, psoriasis and other diseases.

Terms and Definitions

The term "aberrant activity" of cytokine herein means the activity that is significantly different from a base level of the activity of the cytokine in the body in the absence of pathology. The aberrant activity may be caused by excessive cytokine production, the abnormality of processes related to cytokine degradation, and also other factors.

The term "Compound 1" refers to compound 1-(2-(1H-imidazol-4-yl)ethyl)piperidine-2,6-dione, that is also represented by the structural formula:

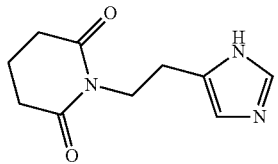 [SMILES: O=C1CCCC(=O)N1CCc1cnc[nH]1]

The term "pharmaceutically acceptable salts" or "salt" includes salts of active compounds which are prepared with the aid of relatively non-toxic acids. Examples of pharmaceutically acceptable non-toxic salts include salts formed by inorganic acids such as hydrochloric acid, hydrobromic acid, phosphoric acid, sulfuric acid and perchloric acid, or organic acids such as acetic acid, oxalic acid, maleic acid, tartaric acid, succinic acid, citric acid or malonic acid, or obtained by other methods used in the field of art. Other pharmaceutically acceptable salts are adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanate, hexanate, hydroiodide, 2-hydroxy-ethanesulfonate, lactobionate, lactate, laurate, lauryl sulfate, malate, maleate, malonate, methanesulfonate (mesylate), 2-naphthalenesulfonate, nicotinate, nitrate, oleate, oxalate, palmitate, pamoate, pectinate, persulfate, 3-phenylpropionate, phosphate, picrate, pivalate, propionate, hemi-fumarate, stearate, succinate, sulfate, tartrate, thiocyanate, p-toluenesulfonate (tosylate), undecanoate, valerate and the like.

The term "solvate" is used to describe a molecular complex containing the compound according to the invention and one or more molecules of a pharmaceutically acceptable solvent, e.g. ethanol.

The term "glutaminyl cyclase" means an enzyme—aminoacyl transferase involved in the conversion of N-terminal glutamine to pyroglutamine in various peptide substrates. The formation of the N-terminal pyroglutamate protects the biologically active peptides, hormones and chemokines from degradation by exopeptidases and in some cases may increase the affinity of ligands to their receptors.

Terms "treatment", "therapy" encompass the treatment of pathological conditions in mammals, preferably in human, and include: a) reducing, b) blocking (suspending) of the disease course, b) alleviating the severity of the disease, i. e. inducing the regression of the disease, d) reversing the disease or condition, to which the term is applied, or one or more symptoms of the disease or condition.

The term "prophylaxis", "prevention" encompasses the elimination of risk factors, as well as the prophylactic treatment of sub-clinical stages of the disease in mammals, preferably, in human, directed to reducing the likelihood of origin of clinical stages of the disease. Patients for the prophylactic therapy are selected based on factors which, on the basis on known data, involve the increase in the risk of origin of clinical stages of the disease as compared with the total population. The prophylactic therapy includes a) primary prophylaxis and b) secondary prophylaxis. The primary prophylaxis is defined as the prophylactic treatment in patients who have not yet reached the clinical stage of the disease. The secondary prophylaxis is the prevention of the repeated onset of the same or close clinical state of the disease.

Compound 1, which is the object of the present invention, is promising for the treatment of pain syndrome, fever, pneumonia, bronchitis, bronchiolitis, alveolitis, rheumatoid arthritis and psoriasis. In some embodiments of the invention, the compound of the invention can be used to prevent or reduce the expression of fever, to normalize the temperature, and alleviate pain.

Method of Therapeutical Use of Compounds

The object of the present invention further comprises administering to a subject in need thereof a therapeutically effective amount of the compound of the invention. The therapeutically effective amount means such an amount of a compound administered or delivered to a patient, upon which the patient is most likely to develop the desired response to the treatment (prophylaxis). The precise required amount may vary from subject to subject depending on the age, body weight and general patient's condition, the severity of disease, the procedure of administration of the preparation, the combined treatment with other preparations and the like.

The compound according to the invention or a pharmaceutical composition comprising the compound can be introduced into the patient's body in any amount and by any way of administration under the condition that such a dose and such a way of the administration are effective for the treatment or prevention of the abovementioned diseases. The oral way of the administration is preferable. Preferably, the daily dose of the active ingredient (the compound according to the invention) is from 0.01 to 0.2 g for a patient per day, the most preferably the daily dose is from 100 to 200 mg/day.

After mixing the required amount of the compound according to the invention (to provide the required dosage) with a pharmaceutically acceptable carrier, medicaments (pharmaceutical compositions) according to the invention can be administered to the body of humans or other animals orally, parenterally, topically, and the like.

The administration may take place both once and several times a day, a week (or at any other time interval), or time from time, as needed. Besides, the medicament (pharmaceutical composition) according to the invention can be administered to the patient's body daily for a certain period of time (that is, e.g., 5-90 days) followed by a period without the administration of the medicament (pharmaceutical composition) according to the invention (that is, e.g., 1-30 days).

When the medicament containing the compound according to the invention is used as the part of combination therapy regimen, the dose of each of components of the combination therapy is administered during the required treatment period. The compounds constituting the combination therapy can be administered to the patient's body both at a time, in the dosage form containing all the components, and in the form of individual dosages of the components.

Use of Compound 1 in the Combination Therapy

Although Compound 1 of the present invention can be administered as an individual active pharmaceutical agent, it can also be used in combination with one or more other agents, in particular, the other agent may be a non-steroidal anti-inflammatory preparation, a glucocorticosteroid, a monoclonal antibody, etc. In case of the combination intake, therapeutic agents may be different dosage forms, which are administered simultaneously or sequentially at different times, or the therapeutic agents can be combined in a single dosage form.

The phrase "combination therapy" in respect to the compound of the present invention in combination with other pharmaceutical agents is the simultaneous or sequential administration of all agents that would otherwise provide beneficial effect of the combination of medicaments. The co-administration implies, in particular, co-delivery, e.g. in one tablet, capsule, injection or other form, having a fixed ratio of active agents, as well as the simultaneous delivery in several separate dosage forms for each compound, respectively.

Thus, the administration of the compound of the present invention may be carried out in combination with additional methods of treatment, known to those skilled in the field of the prophylaxis and treatment of corresponding diseases, comprising the use of antibacterial and cytostatic preparations for the suppression of symptoms or side effects of one of medicaments.

If the dosage form is a fixed dose, the combination uses compounds of the present invention in a suitable dosage range. Compound 1 according to the present invention can also be administered to a patient's body in series with other agents, when the combination of these preparations is impossible. The invention is not limited to the sequence of administration; the compound of the invention may be administered to the patient's body together, before or after the administration of the other preparation.

EXAMPLES

The Preparation of the Compound According to the Invention

The preparation of Compound 1 that is the object of the present invention is described in the invention application WO 2014/168522.

Study of the Effect of Compound 1 on the Enzymatic Activity of Human Glutaminyl Cyclase In Vitro.

During studies of the effect of Compound 1 that is the object of the present invention on the enzymatic activity of glutaminyl cyclase in vitro, the direct inhibitory effect of Compound 1 on recombinant intracellular human glutaminyl cyclase was first discovered.

The activity of glutaminyl cyclase at various concentrations of Compound 1 was studied at 25° C. using the fluorescent substrate L-glutaminyl 2-naphthylamide (Gln-bNA) (Anal Biochem. 2002 Apr. 1; 303(1):49-56). The 100 μl reaction mixture contained 50 μM of a fluorogenic substrate; —0.2 units of human pyroglutaminyl aminopeptidase (1 unit is defined as the amount that hydrolyzes 1 micromole of pGlu-bNA per minute) and an aliquot of recombinant intracellular human glutaminyl cyclase (gQC) in 50 mM of tris-aminomethane-HCl and 5% glycerol, pH is 8.0. The reaction was initiated by adding to the reaction mixture an aliquot of glutaminyl cyclase incubated with Compound 1 for 5 minutes. The further reaction proceeding was monitored spectrophotometrically (the length of the excitation and emission wave was 320 and 410 nm). The enzymatic activity was determined by the amount of the released 2-naphthylamide (bNA) calculated according to a calibration curve. IC50 values were calculated by a nonlinear regression of the "inhibitor concentration"–"enzyme activity" curve. As a comparative substance, the known glutaminyl cyclase inhibitor—Compound PBD150 (J Med Chem. 2006 Jan. 26; 49(2):664-77) was used.

As a result of the experiment, it has been established that Compound 1 inhibits the activity of intracellular glutaminyl cyclase with $IC50=50.9$ μM.

Study of the Activity of Compound 1 on a Mouse Model of Psoriasis.

The induction of psoriasis in mice was carried out according to the standard procedure [European Journal of Pharmacology. 2015. V. 756. P. 43-51]. Aldar cream (5% imiquimod) was applied to female Balb/c mice on the inner side of the right ear once daily by 30 mg/mouse for 7 days (0-6$^{th}$ day). Vaseline was applied to the intact animals. Compound 1 and the reference preparation (neotigason) were administered to animals in an intragastrical way, daily, once per day for 7 days (0-6th day). Euthanasia was carried out 24 hours later (7$^{th}$ day) after the last application of the Aldar cream. Daily on the 0, 2$^{nd}$, 3$^{rd}$, 4$^{th}$, 5$^{th}$, 6$^{th}$ day, the thickness of the right ear was measured in the morning before the next application of the Aldar cream and before the euthanasia. After the euthanasia, blood was collected from the heart cavities, serum was isolated. The content of MCP1 was determined in blood serum by an enzyme-linked immunosorbent assay method, using test systems Mouse CCL2 (MCP-1) Uncoated ELISA Kit (Invitrogen).

The evaluation of the clinical signs of psoriasis was carried out according to the point scale presented in table 1 [Pharmacology. 2011. V. 88(1-2). P. 100-113].

TABLE 1

The system for assessing clinical signs of psoriasis development in mice

| Score | Percentage of the ear exposed to the change | | |
|---|---|---|---|
| | Erythema (reddening) | Flakes | Thickening |
| 0 | None | None | None |
| 1 | 0-25 | 0-25 | 0-25 |
| 2 | 25-50 | 25-50 | 25-50 |
| 3 | 50-75 | 50-75 | 50-75 |
| 4 | 75-100 | 75-100 | 75-100 |

The results of the study showed that on the psoriasis model the intragastric administration of Compound 1 to mice significantly reduces the gain of the ear thickness, clinical signs of psoriasis—the formation of erythema, the thickening of the skin and the formation of flakes on the skin, as well as the MCP-1 level in the blood serum (Tables 2-4).

These results show the therapeutic effect of Compound 1 in case of psoriasis. The therapeutic effect starts already on the 2$^{nd}$ day of the application of Compound 1 and, by the intensity of action, corresponds to or exceeds that of neotigason.

TABLE 2

The gain of the thickness of the affected ear at the determined day of study to day 0 in the mouse model of psoriasis, % (M ± m, n = 20)

| Group | A dose of compound, mg/kg | The gain of the ear thickness at the determined day of study to day 0, % | | | | |
|---|---|---|---|---|---|---|
| | | Day 2 | Day 3 | Day 4 | Day 5 | Day 6 |
| Intact | — | 6.0 ± 1.5 | 7.5 ± 2.5 | 12.3 ± 2.1 | 13.4 ± 1.7 | 16.5 ± 2.0 |
| Control | — | 27.6 ± 1.1* | 35.3 ± 1.1* | 65.3 ± 1.3* | 76.4 ± 2.9* | 95.1 ± 3.1* |
| Compound 1 | 30 | 7.8 ± 1.4& | 11.2 ± 1.9& | 33.8 ± 1.6& | 46.9 ± 1.6*& | 55.8 ± 0.8*& |
| Neotigason | 5 | 14.2 ± 1.9*& | 27.5 ± 1.8*& | 45.9 ± 2.5*& | 68.9 ± 1.8* | 83.1 ± 1.4* |

Notes:
*the distinction from the intact group according to Student's t-test at $p < 0.05$
&the distinction from the control group according to Student's t-test at $p < 0.05$

TABLE 3

Evaluation of the clinical signs of psoriasis on
the mouse model, points (M ± m, n = 20)

| Group | A dose of compound, mg/kg | Day 4 | | | Day 6 | | |
|---|---|---|---|---|---|---|---|
| | | Erythema | Flakes | Thickening | Erythema | Flakes | Thickening |
| Intact | — | 0.0 ± 0.0 | 0.0 ± 0.0 | 0.0 ± 0.0 | 0 ± 0 | 0 ± 0 | 0 ± 0 |
| Control | — | 3.0 ± 0.2* | 1.1 ± 0.2* | 2.5 ± 0.2* | 3.3 ± 0.2* | 1.7 ± 0.2* | 2.6 ± 0.2* |
| Compound 1 | 30 | 1.5 ± 0.1*& | 0.0 ± 0.0& | 0.9 ± 0.1*& | 1.3 ± 0.1*& | 0.1 ± 0.1& | 1.3 ± 0.1*& |
| Neotigason | 5 | 1.2 ± 0.1*& | 0.0 ± 0.0& | 1.4 ± 0.1*& | 1.6 ± 0.1*& | 0 ± 0& | 1.3 ± 0.1*& |

Notes:
*the distinction from the intact group according to Student's t-test at $p < 0.05$
&the distinction from the control group according to Student's t-test at $p < 0.05$

TABLE 4

The MCP-1 level in blood serum of mice on the psoriasis
model, pg/ml (M ± m, n = 10)

| Group | A dose of compound, mg/kg | MCP-1, pg/ml |
|---|---|---|
| Intact | — | 104.6 ± 7.8 |
| Control | — | 172.5 ± 18.5* |
| Compound 1 | 30 | 113.7 ± 8.3 & |

Notes:
*the distinction from the intact group according to Student's t-test at $p < 0.05$
& - the distinction from the control group according to Student's t-test at $p < 0.05$ The Study of the Activity of Compound 1 on the Macrophage and Neutrophil Chemotaxis Model in the Site of Inflammation (Carrageenan Pouch) in Mice The induction of macrophages and neutrophils chemotaxis to the site of inflammation (carrageenan pouch) in mice was tested according to the standard procedure [Curr Protoc Pharmacol. 2012. V. 5. P. 5-6]. Female Balb/c mice, six days before induction of inflammation, were placed in the $CO_2$ chamber until anesthesia was reached for 30 seconds, then 5 ml of air was injected subcutaneously to animals into the intracapsular area of the back by a sterile syringe filled with air. After 3 days to maintain the integrity of the air pouch without increasing the wound, 2.5 ml of air was introduced at the same site. On day 6 under $CO_2$ anesthesia to induce inflammation, 1 ml of 1% carrageenan solution prepared in physiological saline was administered directly into the pouch. The test compound was administered intragastrically 1 hour before the administration of carrageenan and then every 10-12 hours in the volume of 0.1 ml. The last administration is 12 hours before the slaughter. Euthanasia by the inhalation of $CO_2$ was performed 48 hours after the carrageenan injection. Immediately after the euthanasia, 1 ml of physiological saline containing 5.4 mM of EDTA of room temperature was introduced into the pouch with a sterile syringe. After gentle massage of the region of the air pouch, a sagittal incision was made across the pouch and exudate was collected by a dispenser. After the centrifugation of the exudate from the cell pellet, smears were prepared, which were then fixed in methanol and were stained by Romanowsky-Giemsa. A quantity of macrophages and neutrophils was then determined on the smears under a microscope. The cell calculation was made up to 100 pcs.

The results of the study showed that the introduction of carrageenan into the cavity of the air pouch caused the influx of neutrophils and macrophages to the inflammation site (Table 5). Thus, the chemotaxis model of neutrophils and macrophages is formed.

The intragastric administration of Compound 1 to animals reduced the quantity of neutrophils and macrophages in the pouch cavity to the level of intact animals. Thus, the results obtained provide grounds to conclude that Compound 1 prevents chemotaxis of neutrophils and macrophages (Table 5).

TABLE 5

A quantity of inflammation cells in the exudate from
the carrageenan pouch on the neutrophil and macrophage
chemotaxis model to the site of inflammation (carrageenan
pouch) in mice, ×10$^9$/l (M ± m, n = 10)

| Group | A dose of compound, mg/kg | Neutrophils, ×10$^9$/l | Macrophages, ×10$^9$/l |
|---|---|---|---|
| Intact | — | 0.3 ± 0.1 | 0.6 ± 0.1 |
| Control | — | 2.2 ± 0.4* | 7.7 ± 1.5* |
| Compound 1 | 30 | 0.6 ± 0.1 & | 0.6 ± 0.2 & |

Notes:
*the distinction from the intact group according to Student's t-test at $p < 0.05$;
& - the distinction from the control group according to Student's t-test at $p < 0.05$.

Study of the Activity of Compound 1 on a Mouse Model of the Macrophage Chemotaxis to the Site of Inflammation (Thioglycolate Peritonitis)

The induction of macrophage chemotaxis to the site of inflammation (thioglycolate peritonitis) in mice were performed according to the standard procedure [J Leukoc Biol. 2009. V. 86.(2). P. 361-370]. Male Balb/c mice were intraperitoneally administered with 2 ml of 3% thioglycolic medium stored for 1 month. The preparation of thioglycolic medium was carried out as follows: 15 g of dry thioglycolic medium was stirred in 500 ml of distilled water, was boiled at 100° C. for 2 minutes, was filtered through a paper filter, was poured out by 50 ml in sterile tubes and was sterilized by autoclaving at 121° C. for 15 minutes.

The intact animals were intraperitoneally administered with 2 ml of physiological saline. The test compound was intragastrically administered 1 hour before the administration of thioglycolate, 24 and 48 hours after the administration of thioglycolate.

After 72 hours, the animals were euthanized in a $CO_2$-chamber and the peritoneum area was wetted with 70% alcohol, the skin on the abdominal cavity was carefully cut off, and 5 ml of a cold phosphate-saline buffer containing 0.1% of ethylenediamine tetraacetic acid was injected intraperitoneally with a syringe. After gentle massage of the abdominal cavity, the exudate was collected by a syringe into tubes, and the volume of the collected exudate was determined.

Smears were prepared from the cell pellet, which smears were further fixed in methanol (5 minutes) and stained by Romanowsky-Giemsa (40 min at 20-22° C.). On the smears, under the microscope Olympus bx51 (at magnification 100) the quantity of monocytes/macrophages was counted by the routine method. The cell calculation was made up to 100 pcs.

The results of the study have showed that intraperitoneal administration of the thioglycolic medium have caused the apparent increase in the quantity of macrophages in the peritoneal exudate of mice (Table 6). Thus, the macrophage chemotaxis model is formed.

The intragastric administration of Compound 1 to animals reduced the quantity of macrophages in the peritoneal exudate of mice to the level of intact animals. Thus, the obtained results provide groups to conclude that Compound 1 prevents the chemotaxis of macrophages to the site of inflammation (Table 6).

TABLE 6

The quantity of macrophages in peritoneal exudate on the macrophage chemotaxis model to the site of inflammation (thioglycolate peritonitis) in mice.

| Group | A dose of compound, mg/kg | Macrophages, $\times 10^9/l$ |
|---|---|---|
| Intact | — | 0.84 ± 0.16 |
| Control | — | 2.81 ± 0.21* |
| Compound 1 | 30 | 0.84 ± 0.16 & |

Notes:
*the distinction from the intact group according to Student's t-test at $p < 0.05$;
& - the distinction from the control group according to Student's t-test at $p < 0.05$.

passed through the alcohols of ascending concentrations to xylene, and embedded in paraffin by standard procedures. Deparaffinated 5-micron shears were stained with hematoxylin-eosin and the histological analysis was carried out.

Each lesion was evaluated according to a 5-point scale: 1 point—the inflammatory infiltrate occupies 0-20% of the area of the histological preparation under study, 2 point—the inflammatory infiltrate occupies 21-40% of the area of the histological preparation under study, 3 points—the inflammatory infiltrate occupies 41-60% of the area of the histological preparation under study, 4 points—the inflammatory infiltrate occupies 61-80% of the area of the histological preparation under study, 5 points—the inflammatory infiltrate occupies 81-100% of the area of the histological preparation under study. Alveolar destruction index (DI) as the percentage of the damaged alveoli relative to the total number of alveoli was also calculated.

The results of the study showed that multiple intraperitoneal administration of the cigarette smoke extract to mice induces the formation of perivasculitis, peribronchitis, alveolitis and interstitial pneumonia (Table 7).

The intragastric administration of Compound I significantly reduced the development of perivasculitis, peribronchitis, alveolitis and interstitial pneumonia (Table 7). The obtained results make it possible to conclude that Compound I will have the therapeutic effect in case of bronchitis, bronchiolitis, alveolitis and interstitial pneumonia.

TABLE 7

Results of the histological study on the model of non-infectious pneumonia induced by cigarette smoke extract (M ± m, n = 12)

| Group | A dose of compound, mg/kg | Perivasculitis, points | Peribronchitis, points | Alveolitis (DI, %) | Interstitial pneumonia, points |
|---|---|---|---|---|---|
| Intact | — | 0.71 ± 0.20 | 0.51 ± 0.19 | 11.5 ± 1.2 | 0.99 ± 0.20 |
| Control | — | 1.50 ± 0.24* | 1.29 ± 0.18 | 30.9 ± 2.3* | 1.81 ± 0.27* |
| Compound I | 30 | 1.03 ± 0.11& | 0.13 ± 0.07& | 20.5 ± 2.5*& | 1.08 ± 0.16& |

Notes:
*the distinction from the intact group according to Student's t-test at $p < 0.05$;
&the distinction from the control group according to Student's t-test at $p < 0.05$.

The Study of the Activity of Compound 1 on the Model of Non-Infectious Pneumonia Induced by Cigarette Smoke Extract The induction of non-infectious pneumonia in mice was carried out according to the standard procedure [Zhang Yl, Cao J, Chen Y, Chen P, Peng H, Cai S, Luo H, Wu SJ. Intraperitoneal injection of cigarette smoke extract induced emphysema, and injury of cardiac and skeletal muscles in BALB/C mice. Exp Lung Res. 2013 February; 39(1):18-31.] Male Balb/c mice were intraperitoneally administered with cigarette smoke extract (CSE, 0.45 ml/20 mg) at 0, $11^{th}$, $15^{th}$, $17^{th}$, $19^{th}$ and $22^{nd}$ day. The CSE was prepared as follows: 5 cigarettes were burnt, using a vacuum pump, the smoke was filtered to remove particles and collected in a vessel containing a phosphate saline buffer. Compound 1 was administered intragastrically, daily, once a day from $7^{th}$ to $27^{th}$ day. Euthanasia was carried out on the $28^{th}$ day. The right lung lobe was fixed in 10% neutral formalin solution, The Study of the Activity of Compound 1 on a Non-Infectious Pneumonia Model Induced by Intranasal Administration of Poly I:C to Mice The induction of pneumonia in mice was carried out according to the standard procedure [Eur Respir J. 2013 V. 41(5). P. 1147-1156]. Female Balb/c mice were intranasally administered with 8 µg/kg of polyinosine-polycytidylic acid (poly I:C) in 30 µl of PBS on days 1, 2, 3 and 4. Then at days 15, 16, 17 and 18, in the same volume 2 µg/kg of poly I:C were administered to the animals. Compound 1 was administered intragastrically, daily, once a day from day 6 to day 19. All mice were sacrificed on the $19^{th}$ day of the study. The bronchus from the right lung was pinched by the ligature, the left lung was washed 3 times with 0.8 ml of the sterile PBS. After each administration of PBS into the lung, the gentle massage of the lung was carried out, PBS was drained by gravity. Finally, the final volume of the resulting bronchoalveolar lavage (BAL) was considered and written. A number of neutrophils was evaluated in the BAL (using the Diff-Quik staining). For histological study, the right lung lobe was fixed in 10% neutral formalin solution and embedded in paraffin by the standard procedure. Deparaffinated 5-micron shears were stained with hematoxylin-eosin. Each lesion was evaluated according to a 5-point scale: 1 point—the inflammatory infiltrate occupies 0-20% of the area of the histological preparation under study, 2 point—the inflammatory infiltrate occupies 21-40% of the area of the histological preparation under study, 3 points—the inflammatory infiltrate occupies 41-60% of the area of the histological preparation under study, 4 points—the inflammatory infiltrate occupies 61-80% of the area of the histological preparation under study, 5 points—the inflammatory infiltrate occupies 81-100% of the area of the histological preparation under study. Alveolar destruction index (DI) as the percentage of the damaged alveoli relative to the total number of alveoli was also calculated.

The results of the study have shown that the multiple nasal administration of poly I:C to mice induces the influx of neutrophils into the bronchoalveolar space, the formation of perivasculitis, peribronchitis, alveolitis and interstitial pneumonia (Tables 8-9).

The intragastric administration of Compound 1 has completely abolished the influx of neutrophils into the bronchoalveolar space, has significantly reduced the development of perivasculitis, peribronchitis, alveolitis and interstitial pneumonia (Tables 8-9).

TABLE 8

The quantity of neutrophils in the bronchoalveolar lavage on the model of non-infectious pneumonia induced by intranasal administration of poly I:C to mice (M ± m, n = 7)

| Group | A dose of compound, mg/kg | Neutrophils in 1 µl Score |
|---|---|---|
| Intact | — | 0.0 ± 0.0 |
| Control | — | 39.8 ± 36.0* |
| Compound 1 | 30 | 0.0 ± 0.0& |

Notes:
*the distinction from the intact group according to Student's t-test at $p < 0.05$;
&the distinction from the control group according to Student's t-test at $p < 0.05$.

TABLE 9

Results of histological study of the lung tissue on a model of non-infectious pneumonia induced by intranasal administration of poly I:C to mice (M ± m, n = 7)

| Group | A dose of compound, mg/kg | Perivasculitis | Peribronchitis | Alveolitis (DI, %) | Interstitial pneumonia |
|---|---|---|---|---|---|
| Intact | — | 0.36 ± 0.18 | 0.43 ± 0.20 | 10.3 ± 1.7 | 0.57 ± 0.20 |
| Control | — | 1.57 ± 0.37* | 1.71 ± 0.29* | 21.5 ± 2.6* | 1.43 ± 0.3* |
| Compound 1 | 30 | 0.80 ± 0.31& | 0.73 ± 0.32& | 11.5 ± 1.5& | 0.76 ± 0.1& |

Notes:
*the distinction from the intact group according to Student's t-test at $p < 0.05$;
&the distinction from the control group according to Student's t-test at $p < 0.05$.

The obtained results provide grounds to conclude that Compound 1 has the therapeutic effect in case of bronchitis, bronchiolitis, alveolitis and interstitial pneumonia.

The Study of the Activity of Compound 1 on the Model of Fever in Rats

The fever model was realized according to the standard procedure [Tomazzeti J., A'vila D. S., Ferreira A. P. O., Martins J. S., Souza F. R., Royer C. Baker's yeast-induced fever in young rats: characterization and validation of an animal model for antipyretics screening//J Neurosci Methods. 2005. V. 147. P. 29-35]. Wistar rats were injected subcutaneously with 20% Baker's yeast (12 ml/kg). The test compound was administered twice, intragastrically, 2 hours and 14 hours after the yeast administration. The rectal temperature was measured by the electrothermometer before the administration of pyrogen and at the highest point of the development of the thermal response—after 18 hours after it.

The results of the study showed that the intragastric administration of Compound 1 has reduced the body rectal temperature gain of rats (Table 10). The obtained data allow to conclude that Compound 1 has the anti-pyrogenic effect.

TABLE 10

The body rectal temperature gain after 18 hours after the subcutaneous administration of yeast to rats, ° C. (M ± m, n = 10)

| Group | A dose of compound, mg/kg | The body rectal temperature gain, ° C. |
|---|---|---|
| Intact | — | 0.06 ± 0.04 |
| Control | — | 1.67 ± 0.14* |
| Compound 1 | 18 | 1.15 ± 0.12*& |

Notes:
*the distinction from the intact group according to Student's t-test at $p < 0.05$;
&the distinction from the control group according to Student's t-test at $p < 0.05$.

Study of the Activity of Compound 1 on a Model of Specific Pain Reaction by the Method of Chemical Stimulation of Peritoneum ("Abdominal Constriction" Test.)

The model of the specific pain reaction by the method of chemical stimulation of peritoneum ("abdominal constriction" test) was carried out according to the standard procedure. To conduct the "abdominal constriction" test, Balb/c mice were intraperitoneally administered with 1% acetic acid in a volume of 10 ml per kg of the animal body weight. The test compound was administered intragastrically, once, 1 or 2 hour(s) before the administration of acetic acid. A quantity of constrictions (convulsive twitching of the abdominal muscles accompanied with stretching hind quarters and arching) was evaluated 15 minutes after the administration of acetic acid.

The results of the study have shown that the intragastric administration of Compound 1 has significantly reduced the quantity of constrictions in mice, caused by intraperitoneal administration of acetic acid (Table 11). The obtained data allow to conclude that Compound 1 has the pronounced analgesic effect.

TABLE 11

The quantity of acetic constrictions on the model of the specific pain reaction by the method of chemical stimulation of peritoneum ("abdominal constrictions" test) (M ± m, n = 12)

| Group | A dose of compound, mg/kg | The administration of preparations | Quantity of constrictions for 15 minutes |
|---|---|---|---|
| control | — | 1 hour before the administration of acetic acid | 36.3 ± 2.1 |
| Compound 1 | 30 | 1 hour before the administration of acetic acid | 23.8 ± 3.7* |
|  | 30 | 2 hour before the administration of acetic acid | 22.7 ± 2.6* |

Notes:
*the distinction from the intact group according to Student's t-test at $p < 0.05$.

Study of the Activity of Compound 1 on the Model of Thermal Pain Irritation "Hot Plate"

The model of thermal pain irritation "hot plate" was carried out according to the standard procedure [Valdman A. V., Ignatov Y. D. Central mechanisms of pain. L.: Nauka, 1976]. The test compound was administered to Balb/c mice intragastrically, once. After 1, 4, 6, 12, 24 hours after the administration of the preparation, the "hot plate" test was carried out. To conduct the "hot plate" test, the mice were placed on the hot plate, the temperature (+55±1° C.) of which is constant. The time of first manifestations of the pain response in mice (paw licking, jumping) was registered and the mean latent time of the threshold of pain sensitivity (TPS, sec) in each group was calculated.

The results of the study have shown that the intragastric administration of Compound 1 by 2 times has increased the threshold of pain sensitivity of mice in the "hot plate" test. The pharmacological effect of Compound 1 lasted for at least 24 hours (Table 12). The obtained data allow to conclude that Compound 1 has the pronounced analgesic effect of prolonged action.

TABLE 12

The threshold of pain sensitivity (TPS) of the model of thermal pain irritation "hot plate", % to the values before the administration of the preparation (M ± m, n = 12)

| Group | A dose of compound, mg/kg | TPS, % to the values before the administration of the preparation | | | | |
|---|---|---|---|---|---|---|
| | | After 1 hours after the administration of the preparation | After 4 hours after the administration of the preparation | After 6 hours after the administration of the preparation | After 12 hours after the administration of the preparation | After 24 hours after the administration of the preparation |
| Control | — | 111.5 ± 6.9 | 116.3 ± 3.8 | 105.6 ± 6.7 | 109.7 ± 8.8 | 108.4 ± 6.0 |
| Compound 1 | 30 | 192.6 ± 12.7* | 205.2 ± 20.3* | 194.2 ± 12.0* | 191.4 ± 19.4* | 234.7 ± 26.1* |
| Ketorol | 15 | 146.4 ± 16.6 | 195.9 ± 30.0* | 176.6 ± 34.0 | 166.5 ± 25.3 | 159.7 ± 22.4 |

Notes:
*the distinction from the intact group according to Student's t-test at $p < 0.05$.

The preparation of dosage forms of 1-(2-(1H-imidazol-4-yl)ethyl)piperidine-2,6-dione (Compound 1)

The dosage forms of Compound 1 or a pharmaceutically acceptable salt thereof for use in accordance with the present invention are prepared by standard procedures, such as, for example, mixing, granulation, dragee formation, dissolution.

Tableted Form

The tableted form is prepared using the following ingredients:

| | |
|---|---|
| Compound 1 or a pharmaceutically acceptable salt thereof | 1-100 mg |
| Potato starch | 20-50 mg |
| Magnesium stearate | 3 mg |
| Aerosil | 1 mg |
| Lactose | up to 300 mg |

The components are mixed and pressed to form tablets each of which weighs 300 mg.

Gelatin Capsules

Compound 1 or a pharmaceutically acceptable salt thereof—100 mg,

Lactose (milk sugar), potato starch, colloidal silicon dioxide (aerosil), magnesium stearate—till the obtainment of a capsule content of 250 mg. The abovementioned ingredients are mixed, granulated; the granules are filled into solid gelatin capsules in an amount of 250 mg Suppositories Suppository Formulation Example

| | |
|---|---|
| Compound 1 or a pharmaceutically acceptable salt thereof | 1-100 mg |
| Cocoa butter | An amount necessary for suppository production |

It is possible, if necessary, to manufacture rectal, vaginal and urethral suppositories with corresponding excipients.

Powder for Preparing the Solution for Injections

Example 1 of the Formulation

| | |
|---|---|
| Compound 1 or a pharmaceutically acceptable salt thereof | 10-100 mg |

As a solvent, 0.9% sodium chloride solution, distilled water, novocaine solution may be used in the preparation of the solution for injections. The drug form—ampoules, vials, syringe-tubes, "insert".

The invention claimed is:

1. A method for treating a disease or condition caused by the aberrant activity of fractalkine and monocyte chemoattractant proteins 1-4 (CCL2, CCL7, CCL8, CCL13), wherein the a disease or condition or symptom is selected from the group consisting of pneumonia, bronchitis, bronchiolitis, alveolitis, an autoimmune disease, pain syndrome, fever and an elevated temperature, in the body, comprising administering to said body an effective amount of 1-(2-(1H-imidazol-4-yl)ethyl)piperidine-2,6-dione:

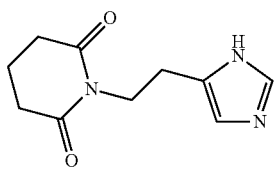 [SMILES: O=C1CCCC(=O)N1CCc1cnc[nH]1]

or a pharmaceutically acceptable salt thereof.

2. The method of claim 1, wherein the dose of 1-(2-(1H-imidazol-4-yl)ethyl)piperidine-2,6-dione or a pharmaceutically acceptable salt thereof is from 0.01 to 0.2 g for a patient per day.

3. The method of claim 2, wherein the dose of 1-(2-(1H-imidazol-4-yl)ethyl)piperidine-2,6-dione or a pharmaceutically acceptable salt thereof is from 0.1 to 0.2 g for a patient per day.

4. The method of claim 1, wherein the autoimmune disease is psoriasis or rheumatoid arthritis.

5. The method of claim 1, wherein the disease or condition or symptom is selected from the group consisting of non-viral pneumonia, non-viral bronchitis, non-viral bronchiolitis, alveolitis, autoimmune disease, pain syndrome, fever, and an elevated temperature.

* * * * *